United States Patent
Nigg et al.

[11] Patent Number: 5,920,601
[45] Date of Patent: Jul. 6, 1999

[54] SYSTEM AND METHOD FOR DELIVERY OF NEUTRON BEAMS FOR MEDICAL THERAPY

[75] Inventors: David W. Nigg; Charles A. Wemple, both of Idaho Falls, Id.

[73] Assignee: Lockheed Martin Idaho Technologies Company, Idaho Falls, Id.

[21] Appl. No.: 08/955,194

[22] Filed: Oct. 21, 1997

Related U.S. Application Data

[60] Provisional application No. 60/029,234, Oct. 25, 1996.

[51] Int. Cl.$^6$ .................................................. G21G 1/10
[52] U.S. Cl. ........................................ 376/194; 376/158
[58] Field of Search ..................... 376/190, 194, 376/156, 158, 112; 350/505.1, 518.1, 251; 600/1

[56] References Cited

U.S. PATENT DOCUMENTS

| | | | |
|---|---|---|---|
| 3,715,597 | 2/1973 | Hofmann et al. | 250/518.1 |
| 3,781,564 | 12/1973 | Lundberg | 250/505.1 |
| 4,112,306 | 9/1978 | Nunan | 376/112 |
| 4,139,777 | 2/1979 | Rautenbach | 376/112 |
| 4,442,352 | 4/1984 | Brahme | 250/251 |
| 4,666,651 | 5/1987 | Barjon et al. | 376/190 X |
| 5,392,319 | 2/1995 | Eggers | 376/194 |
| 5,433,693 | 7/1995 | Ott | 600/1 |
| 5,658,233 | 8/1997 | Peurrung | 600/1 |

FOREIGN PATENT DOCUMENTS 96-00113 1/1996 WIPO.

OTHER PUBLICATIONS

Green, D., et al, *The Financial times Limited; Financial Times,* Mar. 28, 1995.
Menser, P., "I.F. Firm to Market Boron Compounds," *The Post Register,* Idaho Falls, Idaho, May 9, 1996.
Kramer, D., "Brookhaven and Idaho Announce Advances in Cancer Treatment," *Federal Technology Report,* McGraw-Hill, Inc., May 23, 1996.
Maughan et al., A Multirod Collimator for Neutron Therapy, Int. j. Radiation Oncology Biol. Phys., vol. 34, No. 2, pp. 411–420, Jul. 1995.
Zhou et al., Analysis of Epithermal Neutron Production by Near–Threshold (p–n) Reactions, Appl. RAdiat. Isot., vol. 48, No. 10–12, pp. 1571–1575, 1997.

*Primary Examiner*—Daniel D. Wasil
*Assistant Examiner*—M. J. Lattig
*Attorney, Agent, or Firm*—Thorpe North & Western

[57] ABSTRACT

A neutron delivery system that provides improved capability for tumor control during medical therapy. The system creates a unique neutron beam that has a bimodal or multimodal energy spectrum. This unique neutron beam can be used for fast-neutron therapy, boron neutron capture therapy (BNCT), or both. The invention includes both an apparatus and a method for accomplishing the purposes of the invention.

29 Claims, 4 Drawing Sheets

SYSTEM AND METHOD FOR DELIVERY OF NEUTRON BEAMS FOR MEDICAL THERAPY

RELATED APPLICATION

This application claims priority from provisional application Ser. No. 60/029,234 filed Oct. 25, 1996.

CONTRACTUAL ORIGIN OF THE INVENTION

The United States has rights in this invention pursuant to Contract No. DE-AC07-94ID13223 between the U.S. Department of Energy and Lockheed Martin Idaho Technologies Company.

BACKGROUND OF THE INVENTION

1. Field of the Invention

This invention relates to apparatus and methods for delivery of neutron beams for medical therapy. More particularly, it concerns a neutron delivery system with a bimodal energy spectrum that can be used for both fast-neutron therapy and for fast-neutron therapy augmented by boron neutron capture therapy.

2. Background Art

Although the prior art for neutron therapy is voluminous, the prior art fails to disclose the bimodal energy spectrum of the present invention. For example, see the following prior art references:

U.S. Pat. No. 5,392,319, Feb. 21, 1995, Accelerator-based neutron irradiation, Eggers Phillip E., Dublin, Ohio.

U.S. Pat. No. 4,666,651, May 19, 1987, High energy neutron generator, Barjon, Robert, Grenoble, France Breyaat, Genevieve, Brignod, France.

U.S. Pat. No. 4,139,777, Feb. 13, 1979, Cyclotron and neutron therapy installation incorporating such a cyclotron, Rautenbach, Willem L., 18 Unie Ave., Stellenbosh, Cape Province, South Africa.

U.S. Pat. No. 4,112,306, Sep. 5, 1978, Neutron irradiation therapy machine, Nunan, Craig S., Los Altos Hills, Calif.

U.S. Pat. No. 3,781,564, Dec. 25, 1973, NEUTRON BEAM COLLIMATORS, Lundberg, Derek Anthony Hatfield, England.

U.S. Pat. No. 3,715,597, Feb. 6, 1973, ROTATABLE NEUTRON THERAPY IRRADIATION APPARATUS, Hoffmann, Ernst-Gunther, Hamburg, Germany, Federal Republic of Meyerhoff, Kaus, Hamburg, Germany, Federal Republic of Offermann, Bernd Peter, Hamburg, Germany, Federal Republic of Barthel, Rolf, Hamburg, Germany, Federal Republic of Germany.

Application of neutrons for radiotherapy of cancer has been a subject of considerable clinical and research interest since the discovery of the neutron by Chadwick, in 1932. Fast neutron radiotherapy was first used by Robert Stone in the Lawrence Berkeley Laboratory in 1938.

This technology has evolved over the years to the point where it is now a reimbursable modality of choice for inoperable salivary gland tumors, and it is emerging, on the basis of recent research data, as a promising alternate modality for prostate cancer, some lung tumors, and certain other malignancies as well. Neutron capture therapy (NCT), a somewhat different form of neutron-based therapy, was proposed in the mid 1930s and, despite some notable failures in early U.S. trials, has attracted a great deal of renewed research interest lately, due to significant improvements in the relevant technology and radiobiological knowledge.

The basic physical processes involved in fast neutron therapy and neutron capture therapy differ in several respects. In fast neutron therapy, neutrons having relatively high energy (approximately 30–50 MeV) are generated by a suitable neutron source and used directly for irradiation of the treatment volume, just as is done with standard photon (x-ray) therapy. Delivery of fast-neutron therapy for cancer is typically accomplished using accelerator based fast neutron sources that generally involve targeting a proton or deuteron beam onto beryllium. Currently available systems employ various types of cyclotron or liner accelerator technology to deliver the necessary proton beam, which impinges on a suitable target, producing neutrons that are subsequently collimated and delivered to the patient via either a fixed beam delivery system, or by a rotating isocentric structure.

In neutron capture therapy, a neutron capture agent, which in current practice is boron-10 (yielding Boron NCT, or BNCT) is selectively taken into the malignant tissue following the administration of a suitable boronated pharmaceutical, preferably into the bloodstream of the patient. At an appropriate time after boron administration, the treatment volume is exposed to a field of thermal neutrons produced by application of an external neutron beam.

The thermal neutrons interact with the boron-10, which has a very high capture cross section in thermal energy range and which, ideally, is present only in the malignant cells. Each boron-neutron interaction produces an alpha particle and a lithium ion. These highly-energetic charged particles deposit their energy within a geometric volume that is comparable to the size of the malignant cell, leading to a high probability of cell inactivation by direct DNA damage.

Because boron is ideally taken up only in the malignant cells, the NCT process offers the possibility of highly selective destruction of malignant tissue, with cellular-level separating of neighboring normal tissue since the neutron sources used for NCT are, themselves, designed to produce a minimal level of damage of normal tissue.

When BNCT is administered as a primary therapy, an epithermal-neutron beam (neutrons having energies in the range of 1 eV to 10 keV) is used to produce the required thermal neutron flux at depth, since these somewhat higher-energy neutrons will penetrate deeper into the irradiation volume before thermalizing, yet they are still not of sufficient energy to inflict unacceptable damage to intervening normal tissue.

A third form of neutron therapy, which is basically a hybrid that combines the features of fast neutron therapy and NCT is also currently a subject of research interest, and constitutes the field of application where this invention is useful. In this type of radiotherapy, a neutron capture agent is introduced preferentially into the malignant tissue prior to the administration of standard fast neutron therapy.

Because a small fraction of the neutrons in fast neutron therapy will be thermalized in the irradiation volume, it is possible to obtain a small incremental absorbed dose from the neutron capture interactions that result. Improved tumor control relative to fast neutron therapy alone using the augmentation concept is clearly promising based on current radiobiological research. However, until now, no NCT augmentation system has been developed that makes a significant improvement over the unaugmented fast neutron therapy.

Additionally, prior art fast-neutron therapy systems are largely located only at major research centers due to the fact that they are physically complex, bulky and require high-level operating staffs to maintain. In general these systems are not well suited for wide-spread, practical, clinical deployment.

BRIEF SUMMARY AND OBJECTS OF THE INVENTION

The present invention provides a potentially compact, user friendly, field-deployable neutron delivery system with dual capabilities for fast neutron therapy alone, or for fast neutron therapy with neutron capture therapy augmentation, with much improved capability for tumor control during neutron beam treatment.

It is an object of the present invention to provide improved capability for tumor control during medical therapy through means of superior control of a neutron beam.

The present invention is a neutron delivery system that provides improved capability for tumor control by producing a specially tailored neutron beam. The specially tailored neutron beam has a bimodal energy spectrum and provides dramatically enhanced tumor control during medical therapy by allowing neutron therapy to be enhanced with neutron capture therapy. The system includes: a structure for producing a proton beam; at least one target; and a magnet arrangement for directing the proton beam into the at least one target. The target includes layers for producing, when impacted by the proton beam, at least one neutron beam having a bimodal energy spectrum for use with both fast-neutron therapy and boron neutron capture therapy. Finally, the neutron beam passes through a collimator prior to delivery to a patient.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features, and advantages of the invention will become apparent from a consideration of the following detailed description presented in connection with the accompanying drawings in which.

DETAILED DESCRIPTION OF THE PREFERRED EMBODIMENTS

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the appended claims.

In General

Figure 1:
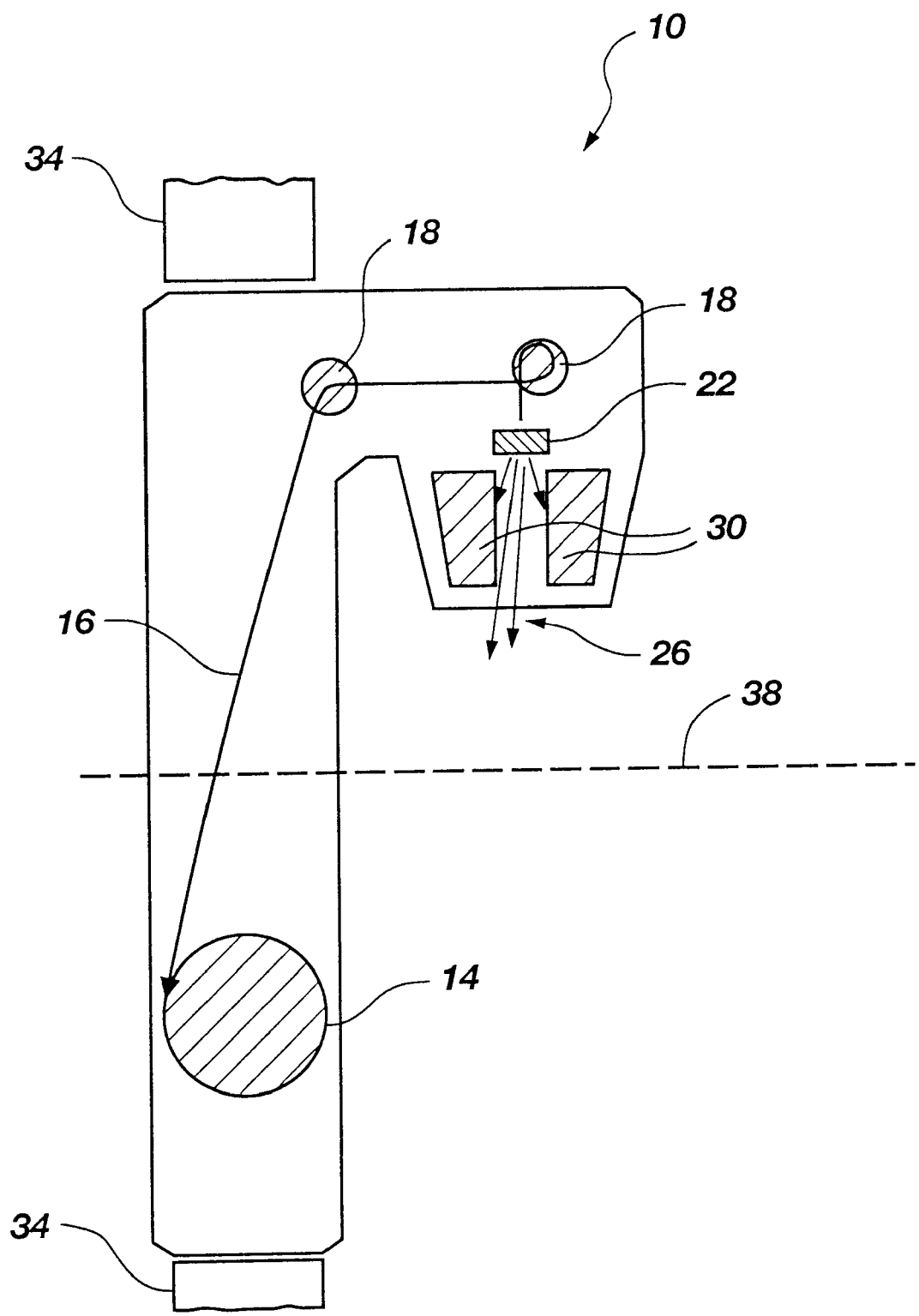
FIG. 1 is a side view of a self-contained gantry mounted neutron delivery system.

A sketch of a proposed system for neutron delivery is shown in FIG. 1. A superconducting cyclotron produces a proton beam, which is subsequently directed through a system of bending magnets to a target assembly where neutrons are produced.

This target assembly is laminated and has other design features to enhance the production of neutrons having a spectrum that will simultaneously induce a desired fast-neutron dose-depth profile in hydrogenous tissue at the isocenter as well as a desired thermal-neutron flux profile in the same hydrogenous target volume at the isocenter. This specially tailored neutron beam is achieved in the present invention by a specially designed accelerator target and/or by selective neutron filtering downstream from the target itself, but within the target assembly shown in FIG. 1.

The preferred target assembly has several elements: first is a proton-neutron conversion region composed in the currently-preferred embodiment of laminated beryllium and tungsten, followed by a neutron filtering subassembly composed of a suitable material having neutron cross-section characteristics such that the downstream spectrum emerging from the filter has an operator adjustable bimodal shape as a function of energy as the result of the action of the target and/or filter. The target filter assembly is followed in turn by suitable flattening and wedge filters, composed in the currently preferred embodiment of tungsten or iron.

Downstream of the target-filter assembly is a multi-segment collimator to further tailor the neutron beam prior to delivery to the patient at the isocenter. As shown, all major components of the system are preferably housed within a balanced rotating structure that can be mounted in a large circular opening in the interior wall of the building where the systems is installed. The mounting wall will generally be quite thick, in order to provide the necessary level of neutron shielding.

The device can be mounted on roller bearings, with a ring gear wrapped circumferentially around the periphery of the housing or circumferentially within the opening within the wall where the system is installed. Either way, small drive motors engage the large ring gear to facilitate rotation of the entire assembly about the isocenter to within the required precision.

Figure 3:
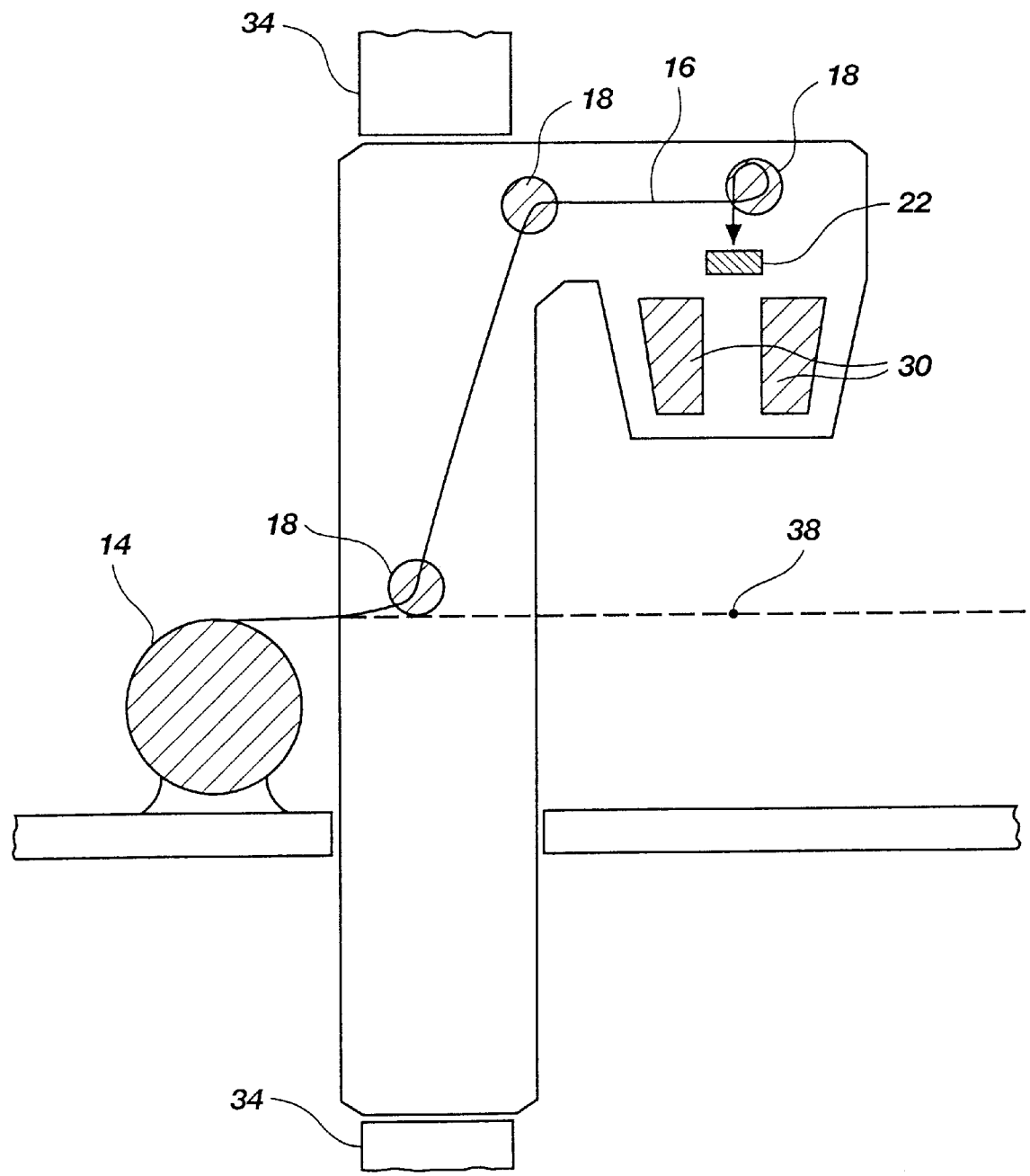
FIG. 3 is a side view of a gantry mounted neutron delivery system with a superconducting cyclotron located just behind the rotating wheel assembly.

An alternative embodiment of this invention is illustrated in FIG. 3. In FIG. 3, the cyclotron itself is located just behind the rotating assembly. This is a less-preferred embodiment at this time because somewhat more space is required. Additionally, the cyclotron could not be used to counterbalance the weight of the target and collimator assembly. Thus, this embodiment requires the installation of additional counterweights in the rotating structure itself.

An alternate approach within this invention is to sequentially expose the target volume of the patient with two or more neutron beams having different energy levels to cumulatively achieve the same result as that achieved by a tailored beam. Ease of treatment will normally make a system having a tailored neutron beam the system of choice.

In Detail

Figure 2:
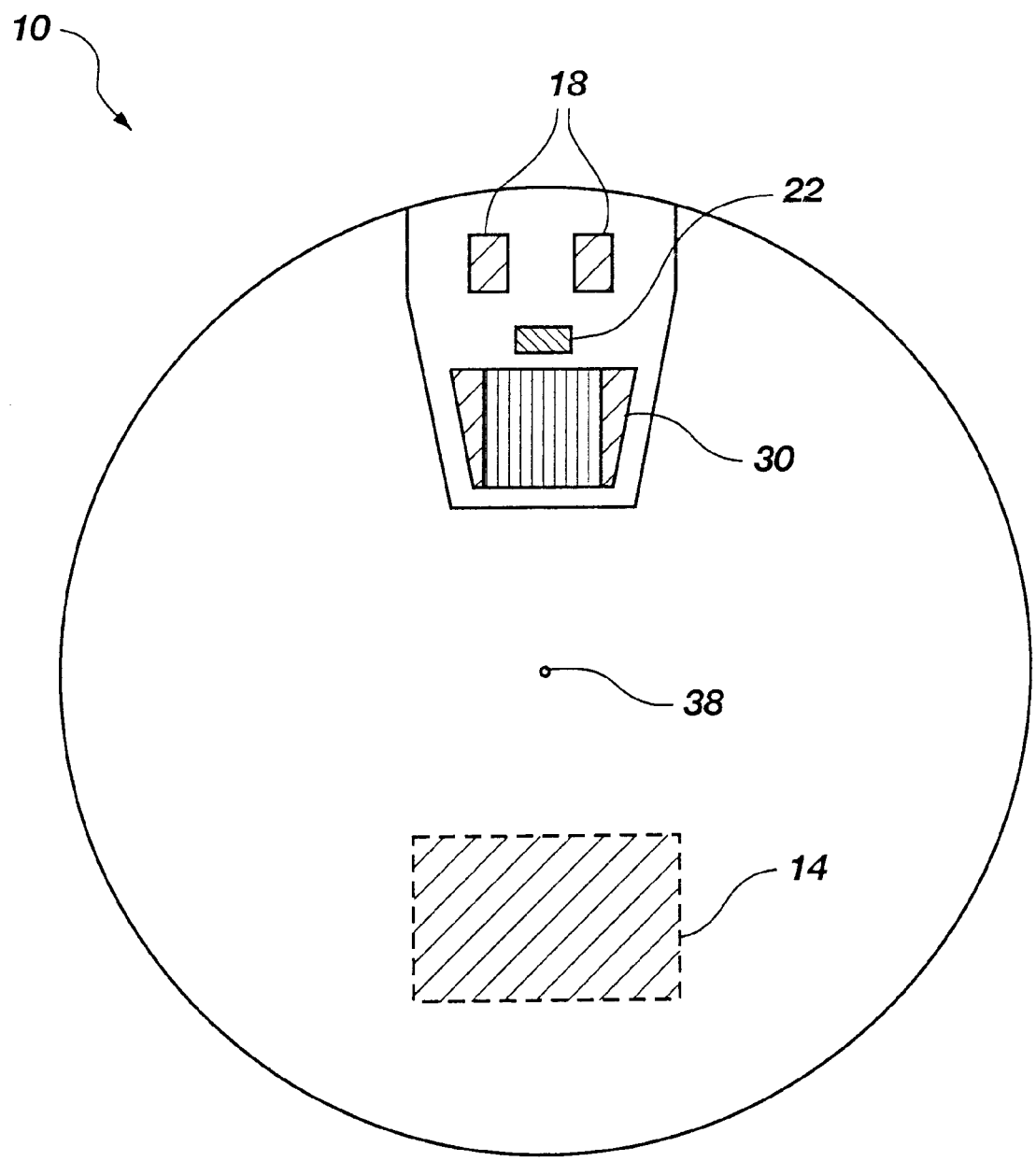
FIG. 2 is an end view of a self-contained gantry mounted neutron delivery system.

As illustrated in FIG. 1 and FIG. 2, a neutron delivery system 10 provides improved capability for tumor control during medical therapy. The neutron delivery system 10 includes the following parts: a cyclotron 14 for producing a proton beam 16; magnets 18; and at least one target 22. The magnets 18 are for directing the proton beam 16 into the target 22 so that the target produces at least one neutron beam 26 when impacted by the proton beam. The neutron beam 26 has a bimodal energy spectrum that can be used with both fast-neutron therapy and boron neutron capture therapy. The delivery system 10 also includes a collimator 30 to further tailor the neutron beam 26 prior to delivery to a patient. The delivery system 10 is housed on a balanced rotating structure 34.

Although the neutron delivery system 10 of FIG. 1 shows a cyclotron 14, the delivery system may have various embodiments. More specifically, the cyclotron 14 of FIG. 1, may be replaced by a compact superconducting cyclotron, or other means for producing a proton or deuteron beam.

However a user chooses to produce the proton beam 16, the neutron delivery system 10 should enable a user to produce proton beams with various energy levels. A preferred energy range of a proton beam is in the 50–70 MeV range. When a proton beam 16 in the 50–70 MeV range is produced, the neutron delivery system 10 typically uses magnets 18 to create a bending magnet system that directs the proton beam 16 into the target 22.

Once the proton beam 16 is directed into the target 22, the target will produce the neutron beam 26. The target 22 is capable of producing at least one neutron beam having a high energy component in the 30–60 MeV range and a low-energy component in the 10 KeV to 2 MeV range.

Figure 4:
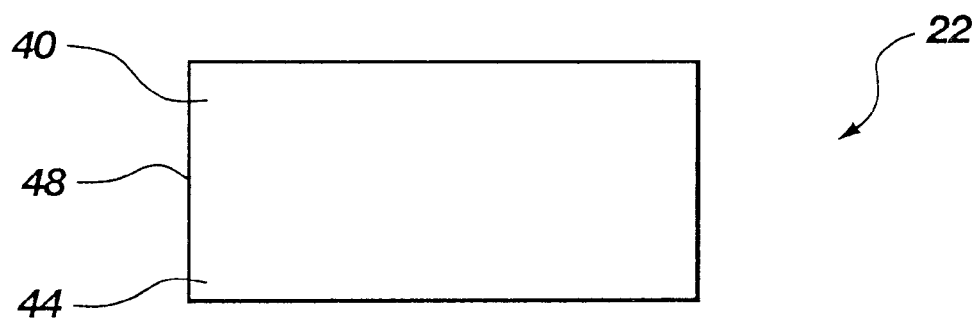
FIG. 4 shows a side view of a target of the present invention where divisions between layers of the target are indicated with dotted lines.

As shown in FIG. 4, the target 22 is composed of a plurality of layers. Although in a preferred embodiment the target 22 has two layers, i.e., a layer of beryllium 40 and a layer of tungsten 44, in another embodiment, the target has a third layer of carbon 48. The layer of beryllium 40 is about five millimeters thick and the layer of tungsten 44 is about four millimeters thick. The layer of carbon may be placed between the two other layers. In addition, rather than a beryllium layer 40, the layer may be made of lithium or other material to produce a neutron beam. Different targets and projectiles will produce different types of neutron sources.

These layers create the bimodal energy effect in the neutron beam(s) when first the beryllium layer 40 and subsequently the tungsten layer 44 of the target 22 are impacted by the proton beam 16. One effect is to cause a single neutron beam to be produced and this is tailored in a manner commonly understood by those skilled in the art to change the spectrum and/or intensity in a desired manner.

In another embodiment, the bimodal effect of the target 22 can be accomplished with a target that has the following combination of layers: a proton-neutron conversion region; a neutron filtering subassembly; a spectral filter for modifying the neutron beam; and a plurality of filters for flattening and wedging purposes.

The proton-neutron conversion region is often made up of a layer of beryllium operably attached to a layer of tungsten. The layer of beryllium can have a thickness of between about 3 to about 10 millimeters while the layer of tungsten can have a thickness of between about 1 to about 7 millimeters. These are only suggested layer thicknesses and are clearly approximations that can be modified and still produce desirable results.

The neutron filtering subassembly is only limited in that it should be made of a material having neutron cross section characteristics such that the beam is modified in a desired manner upon passage through the filtering subassembly. For example if the system is to be used in a particular case for fast-neutron therapy without neutron capture augmentation it may be desirable to preferably attenuate the low-energy component of the bimodal spectrum by use of a filtering subassembly composed of a hydrogeneous material such as polyethylene.

The spectral filter for producing a neutron beam from the neutron filtering subassembly can be adjustable by an operator. The operator has the option of producing a spectrum having a bimodal shape or otherwise.

The tailored neutron beam is typically collimated to transverse dimensions of from 5 to 30 centimeters by from 5 to 30 centimeters. In addition, when the collimated neutron beam impinges on the treatment volume, the half-value depth of the fast-neutron dose profile is typically from 17 to 21 centimeters, and a scalar thermal-neutron fluency field of from 2 to $5 \times 10^{10}$ neutron per square centimeter (2200 meters per second equivalent) per 100 centigrays of fast neutron dose is simultaneously generated at a 5 centimeter depth on-axis. It should be noted that the spectral filter means may also be made of tungsten, bismuth, and/or iron, depending on the desired effect.

The bimodal shape of the spectrum is a function of energy as the result of the action of the target and/or filter.

The filters for flattening and wedging purposes are such that the neutron beam is flattened and tilted.

The plurality of filters for flattening and wedging purposes may be composed of tungsten or iron. The filters may also include a hydrogenous material for reducing the low-energy component of the spectrum. This hydrogenous material is commonly polyethylene.

The collimator 30 of FIG. 1, to further tailor the neutron beam prior to delivery to a patient, may be a multi-segment collimator wherein the neutron beam may be further tailored prior to delivery to the patient. Of course, the beam should be delivered to the patient at an isocenter 18. Additionally, the collimator 30 may be made of iron and/or bismuth.

The neutron delivery system is housed in a balanced rotating structure 34. One possible embodiment for housing the system is a rotating isocentric gantry structure. The gantry structure contains all system components. These components are held in a manner such that the tailored neutron beam from the collimator is easily moved for exposing the target to be treated in different directions. To accomplish this embodiment, the balanced rotating structure for housing the system has numerous parts that must work together.

Figure 5:
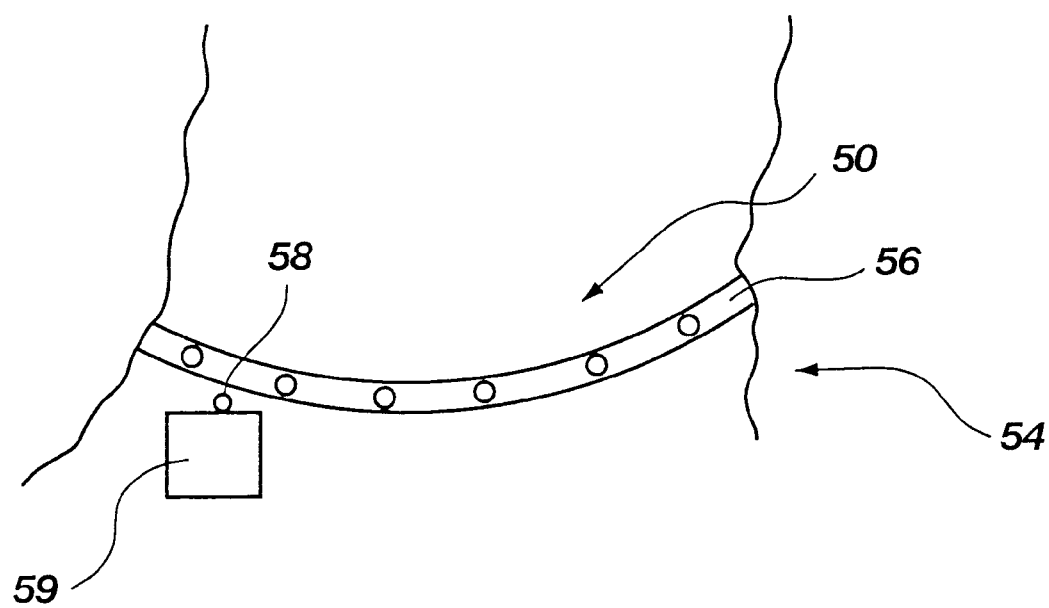
FIG. 5 illustrates a partial front view of a neutron delivery system mounted in a wall, the partial view focusing on the bearings between the housing of the delivery system and the wall, and the ring gear and motor for rotating the housing.

First, as shown in FIG. 5, the structure has a housing 50 that is mounted in a large circular opening in an interior wall 54 of the building where the system is installed. This interior wall 54 is quite thick so that it is capable of neutron shielding and able to support the weight of the structure. Second, the housing 50 is mounted on roller bearings to assist the housing to rotate within the wall 54.

Rotating the housing 50 on the bearings 56 is accomplished with a ring gear 58. The ring gear 58 is wrapped circumferentially around a periphery of the housing 50. The ring gear 58 is operated by at least one is drive motor 59. The drive motor 59 is mechanically coupled to the ring gear 58 to engage the ring gear and facilitate rotation of the balanced rotating structure. The structure as a whole can then be easily rotated about an isocenter 38 (see FIG. 1). One skilled in art and viewing the housing of the present invention would be enabled to make and use the above described ring gear and drive motor for rotating the housing.

The method for using a neutron delivery system to provide improved tumor control capability during medical therapy is accomplished through the following steps: producing a proton beam; directing the proton beam into at least one target; creating at least one neutron beam having a bimodal energy spectrum for use with both fast-neutron therapy and boron neutron capture therapy; tailoring the at least one neutron beam by means of a filter collimator system; delivering the tailored at least one neutron beam to a patient; and housing the system in a balanced rotating structure for ease of adjustment.

This method may be further defined to specify that the step of producing a proton beam comprises producing a proton beam in the 50–70 MeV energy range. This proton beam may be produced with any particle accelerator, e.g., a typical cyclotron or a superconducting cyclotron.

The proton beam is then used to create at least one neutron beam when the proton beam impacts with at least one target. This collision produces a neutron beam that has a bimodal energy spectrum because of the properties of the material in the target. The bimodal energy spectrum is a neutron beam (s) that has neutrons with various energy levels. In other words, at least one neutron beam has a high energy component in the 30–60 MeV range and a low-energy component in the 10 KeV to 2 MeV range.

The method described above may be accomplished by creating a single tailored neutron beam. This single tailored neutron beam is created by exposing a specially designed target with the neutron beam and/or by the use of spectral filters to eliminate or enhance neutrons of certain energies.

The above variations are not inclusive. They are only examples of the preferred embodiments. It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

We claim:

1. A neutron delivery system providing improved capability for tumor control during medical therapy, the system comprising:
    a means for producing a proton beam;
    at least one target;
    a means for directing the proton beam into the at least one target;
    said at least one target comprising means for producing, when impacted by the proton beam, at least one neutron beam having a bimodal energy spectrum for use with both fast-neutron therapy and boron neutron capture therapy; and
    a collimator wherein the at least one neutron beam passes prior to delivery to a patient.

2. The neutron delivery system of claim 1 wherein the means for producing a proton beam comprises a particle accelerator.

3. The neutron delivery system of claim 2 wherein the particle accelerator comprises a cyclotron.

4. The neutron delivery system of claim 3 wherein the cyclotron comprises a compact superconducting cyclotron.

5. The neutron delivery system of claim 1 wherein the means for producing a proton beam comprises means for producing a proton beam in the 50–70 MeV range.

6. The neutron delivery system of claim 1 wherein the means for directing the proton beam into the at least one target comprises a proton beam bending magnet system.

7. The neutron delivery system of claim 1 wherein the at least one target comprises means for producing at least one neutron beam having a high energy component in the 30–60 MeV range and a low-energy component in the 10 KeV to 2 MeV range.

8. The neutron delivery system of claim 1 wherein the at least one target comprises a plurality of layers having means for producing at least one neutron beam that is a single tailored neutron beam with certain energies being suppressed and other energies being enhanced.

9. The neutron delivery system of claim 8 wherein the plurality of layers of the at least one target comprises:
    a proton-neutron conversion region;
    a spectral filter means for producing a neutron beam from the neutron filtering subassembly, the means adjustable by an operator for producing a spectrum having a bimodal shape; and
    a plurality of filters for flattening and wedging purposes wherein the neutron beam is flattened and tilted, the plurality of filters being operator-controlled so that the low-energy component of the neutron beam can be reduced when it is desired to administer fast-neutron therapy alone, without neutron capture therapy augmentation.

10. The neutron delivery system of claim 9 wherein the proton-neutron conversion region comprises a layer of beryllium operably attached to a layer of tungsten.

11. The neutron delivery system of claim 10 wherein the layer of beryllium has a thickness of between about 3 to about 10 millimeters and wherein the layer of tungsten has a thickness of between about 1 to about 7 millimeters.

12. The neutron delivery system of claim 9 wherein the neutron filtering subassembly comprises neutron cross section characteristics suitable for effecting the desired spectral modification of the beam.

13. The neutron delivery system of claim 9 wherein the spectral filter means further tailors the tailored neutron beam into a desired multi-modal spectral shape such that when the neutron beam impinges upon a volume of hydrogenous tissue (the "treatment volume"), the resulting absorbed radiation dose-depth profile induced by such neutrons has a half-value depth of at least from about 17 to about 21 centimeters when such neutron beam is collimated to transverse dimensions of 20 centimeters by 20 centimeters and such that when the collimated neutron beam impinges on the treatment volume a scaler thermal-neutron fluency field of from about 2 to about $5 \times 10^{10}$ neutron per square centimeter (2200 meters per second equivalent) per 100 centigrays of fast neutron dose is simultaneously generated at a 5 centimeter depth on-axis.

14. The neutron delivery system of claim 13 wherein the spectral filter means comprises tungsten, bismuth, and iron, and a hydrogeneous material.

15. The neutron delivery system of claim 9 wherein the bimodal shape of the spectrum is a function of energy as the result of the action of the target and filter.

16. The neutron delivery system of claim 9 wherein the plurality of filters for flattening and wedging purposes are composed of tungsten and iron.

17. The neutron delivery system of claim 16 wherein the plurality of filters for flattening and wedging purposes additionally comprise a hydrogenous material for reducing the low-energy component of the spectrum.

18. The neutron delivery system of claim 17 wherein the hydrogenous material comprises polyethylene.

19. The neutron delivery system of claim 1 wherein the collimator comprises a multi-segment collimator for the neutron beam to pass through prior to delivery to the patient at an isocenter.

20. The neutron delivery system of claim 1 wherein the collimator comprises iron and bismuth.

21. The neutron delivery system of claim 1 wherein a balanced rotating structure houses the system and wherein the balanced rotating structure comprises a rotating isocentric gantry means to contain all system components in a manner such that the neutron beam from the collimator is easily moved for exposing the target to be treated in different directions.

22. The neutron delivery system of claim 21 wherein the balanced rotating structure for housing the system comprises:
  a housing that is mounted in a large circular opening in an interior wall of a building where the system is installed, said housing being mounted on roller bearings within the interior wall;
  said interior wall being providing neutron shielding;
  a ring gear wrapped circumferentially around a periphery of the housing; and
  at least one drive motor mechanically coupled to the ring gear to engage the ring gear and facilitate rotation of the balanced rotating structure, wherein the structure is rotated about an isocenter.

23. A neutron delivery system providing improved capability for tumor control during medical therapy, the system comprising:
  a means for producing a proton beam in the 50–70 MeV energy range;
  a target comprising means for producing a tailored neutron beam having a high-energy component in the 30–50 MeV range and a low-energy component in the 10 KeV to 2 MeV range;
  a means for directing the proton beam onto the target which produces a neutron beam in response to such proton beam/target interaction;
  a spectral filter means immediately downstream of the target and which further tailors the tailored neutron beam into a desired bimodal spectral shape such that when the neutron beam impinges upon a volume of hydrogenous tissue (the "treatment volume"), the resulting absorbed radiation dose-depth profile induced by such neutrons has a half-value depth of at least from about 17.0 to about 21.0 centimeters when such neutron beam is collimated to transverse dimensions of 20 centimeters by 20 centimeters and such that when the collimated neutron beam impinges on the treatment volume a scaler thermal-neutron fluency field of from about 2 to about $5 \times 10^{10}$ neutron per square centimeter (2200 meters per second equivalent) per 100 centigrays of fast neutron dose is simultaneously generated at a 5 centimeter depth on-axis;
  a flattening and wedge filter means downstream of the spectral filter means and having additional components to selectively reduce the low energy component of the neutron beam when it is desired to administer fast-neutron therapy alone, without neutron capture therapy augmentation; and
  a collimator means for directing the one or more neutron beams to a desired target to be treated.

24. A method for using a neutron delivery system to provide improved tumor control capability during medical therapy, the method comprising:
  producing a proton beam;
  directing the proton beam into at least one target;
  creating at least one neutron beam having a bimodal energy spectrum for use with both fast-neutron therapy and boron neutron capture therapy, the at least one neutron beam being created upon impact of the proton beam with the at least one target;
  tailoring the at least one neutron beam by means of a collimator;
  delivering the tailored at least one neutron beam to a patient; and
  housing the system in a balanced rotating structure for ease of adjustment.

25. The method of claim 24 wherein the step of producing a proton beam comprises producing a proton beam in the 50–70 MeV energy range.

26. The method of claim 24 wherein the step of producing a proton beam comprises producing a proton beam with a superconducting cyclotron.

27. The method of claim 24 wherein the step of creating at least one neutron beam having a bimodal energy spectrum comprises creating at least one neutron beam having a high energy component in the 30–70 MeV range and a low-energy component in the 10 KeV to 2 MeV range.

28. The method of claim 24 wherein the step of creating at least one neutron beam comprises creating a single tailored neutron beam by exposing a target means with the neutron beam and by the use of filters to eliminate or enhance neutrons of certain energies.

29. The method of claim 28 further comprising the step of passing the tailored neutron beam through a spectral filter means which further tailors the tailored neutron beam into a desired multi-modal spectral shape such that when the neutron beam impinges upon a volume of hydrogenous tissue (the "treatment volume"), the resulting absorbed radiation dose-depth profile induced by such neutrons has a half-value depth of from at least about 17 to about 21 centimeters when such neutron beam is collimated to transverse dimensions of 20 centimeters by 20 centimeters and such that when the collimated neutron beam impinges on the treatment volume a scaler thermal-neutron fluency field of from about 2 to about $5 \times 10^{10}$ neutron per square centimeter (2200 miles per second equivalent) per 100 centigrays of fast neutron dose is simultaneously generated at a 5 centimeter depth on-axis.

\* \* \* \* \*